(12) United States Patent
Cote et al.

(10) Patent No.: US 6,324,898 B1
(45) Date of Patent: Dec. 4, 2001

(54) METHOD AND APPARATUS FOR TESTING THE INTEGRITY OF FILTERING MEMBRANES

(75) Inventors: Pierre Cote, Dundas; Arnold Janson, Burlington; Nicholas Adams, Hamilton, all of (CA)

(73) Assignee: Zenon Environmental Inc., Oakville (CA)

( * ) Notice: Subject to any disclaimer, the term of this patent is extended or adjusted under 35 U.S.C. 154(b) by 0 days.

(21) Appl. No.: 09/468,779

(22) Filed: Dec. 21, 1999

(51) Int. Cl.⁷ .................................................. G01N 15/08
(52) U.S. Cl. .................................................. 73/38; 210/90
(58) Field of Search .................... 73/38; 210/85, 210/90, 93

(56) References Cited

U.S. PATENT DOCUMENTS

| | | | |
|---|---|---|---|
| 4,231,768 | 11/1980 | Seibert et al. | 55/179 |
| 4,614,109 * | 9/1986 | Hofmann | 73/38 |
| 4,701,861 | 10/1987 | Kauke | 364/502 |
| 4,778,499 * | 10/1988 | Beaver | 65/2 |
| 4,881,176 | 11/1989 | Kononov | 364/500 |
| 5,064,529 | 11/1991 | Hirayama et al. | 210/90 |
| 5,353,630 | 10/1994 | Soda et al. | 73/38 |
| 5,417,101 * | 5/1995 | Weich | 73/38 |
| 5,488,811 | 2/1996 | Wang et al. | 53/52 |
| 5,507,959 * | 4/1996 | Glick | 73/38 |
| 5,594,161 * | 1/1997 | Randhahn et al. | 73/38 |
| 5,783,760 * | 7/1998 | Haines et al. | 73/865.6 |
| 5,786,528 * | 7/1998 | Dileo et al. | 73/38 |
| 5,808,181 * | 9/1998 | Wamseidler et al. | 73/38 |
| 5,888,401 * | 3/1999 | Nguyen | 210/650 |
| 6,022,478 * | 2/2000 | Baurmeister et al. | 210/651 |

FOREIGN PATENT DOCUMENTS

| | | | | |
|---|---|---|---|---|
| 0 139 202 | 5/1985 | (EP) | | G01N/15/08 |
| 0 592 066 | 4/1994 | (EP) | | G01N/15/08 |
| 2 132 366 | 7/1984 | (GB) | | G01N/15/08 |
| 04348252 * | 12/1992 | (JP) | | 73/38 |
| WO 97/45193 | 12/1997 | (WO) . | | |

OTHER PUBLICATIONS

"Journal AWWA", Low Pressure Membranes: Assessing Integrity: Mar. 1995, pp. 62–75.

* cited by examiner

*Primary Examiner*—Hezron Williams
*Assistant Examiner*—Michael Cygan
(74) *Attorney, Agent, or Firm*—Bereskin & Parr

(57) ABSTRACT

An improvement to an outside/in hollow fiber membrane filtration system includes a source of suction on the lumens of the membranes or pressure on the outside of the membranes operable without producing permeate and an air collector to collect any air that passes from the outside of the membranes to their lumens during an integrity test. A method for testing the integrity of filtering membranes involves exposing a first side of the membranes to air while a second side of the membranes remains exposed to water. A transmembrane pressure forces air through defects of concern in the membranes. Air that passes through a set of membranes is collected and its amount measured and compared to an acceptable amount of air to indicate whether there is a defect in the set of membranes. Preferably, air is collected individually from a plurality of membrane units in a filtration train and the amounts so collected compared to indicate if one of the membrane units is defective.

15 Claims, 4 Drawing Sheets

METHOD AND APPARATUS FOR TESTING THE INTEGRITY OF FILTERING MEMBRANES

FIELD OF THE INVENTION

The present invention relates to a method and apparatus for testing the integrity of filtering membranes.

BACKGROUND OF THE INVENTION

Filtering membranes are used to permeate a relatively particle free liquid from a liquid rich in particles. Reverse osmosis and nanofiltration membranes, for example, are used to produce very high quality water for drinking or industrial applications. Ultrafiltration and microfiltration membranes are used at lower pressure to filter water for drinking or industrial applications and to treat waste water.

One reason for using membranes to filter water is that membranes are able to remove very small particles including pathogenic microorganisms and colloids. Thus, strong chemicals may not be required as a primary disinfectant in drinking water applications and a nearly complete lack of colloids in water produced for industrial purposes improves the performance of many industrial processes. To ensure that undesired particles are removed, however, the integrity of a membrane unit must be monitored and tested regularly. In particular, although membranes are usually tested after they are manufactured, leaks can develop when the membranes are installed in a filtering system and during the subsequent operation of the system. For example, leaks may result from fatigue, from over-pressurization, or from cleaning and maintenance activities.

Membrane integrity can be monitored using continuous or discontinuous methods. Continuous integrity testing techniques, which include particle counting and acoustic analysis, do not evaluate the membrane itself but instead monitor and assess a surrogate parameter to diagnose the membrane condition. For instance, a batch or on-line particle counter generally includes a light scattering sensor, typically laser-based, interfaced with a computer running particle enumeration software that assesses the number of particles in one or more particle size ranges: see generally Panglish et al., "Monitoring the Integrity of Capillary Membranes by Particle Counters", *Desalination*, vol. 119, p. 65–72 (1998). Similarly, a particle monitor that measures the fluctuation in intensity in a narrow light beam transmitted through a permeate sample is also known. Through subsequent computer analysis, the observed fluctuations can be converted into an index of water quality. Particle counting and particle monitoring techniques require elaborate and expensive measurement equipment that is subject to measurement drift, noise, and periodic maintenance such as calibration. In addition, these methods generally do not differentiate between undesirable particles and other signals that have no relation to membrane integrity, particularly air bubbles produced on the permeate side of the membrane and associated with backwashing operations. Moreover, the number of membrane units or modules that can be simultaneously monitored using these integrity testing methods is limited by dilution effects.

In acoustic membrane analysis methods, as described in Glucina et al., "Acoustic Sensor; a Novel Technique for Low Pressure Membrane Integrity Monitoring", AWWA Membrane Conference, Long Beach, Calif. (Feb. 28 to Mar. 3, 1999), one or more sound wave sensors or transducers are placed on a membrane unit to detect anomalies in the acoustic response of the membrane, namely noise originating from broken fibres. These acoustic techniques, however, detect only broken fibres and do not detect more subtle defects in, or the general deterioration of, a membrane. Furthermore, these methods are susceptible to interference from surrounding noise and are very expensive, since they require at least one acoustic sensor per membrane unit and each of these sensors must be electrically connected to a central computer for appropriate signal analysis.

In another class of integrity testing techniques, membrane integrity is assessed directly while permeation is temporarily stopped. Typically, air (or another suitable gas) is applied to a first side of a wet membrane at a pressure higher than the pressure of water or air on a second side of the membrane to create a trans-membrane pressure but at a pressure lower than the bubble point of a membrane without defects. A rapid flow of air from the first side of the membrane to the second side indicates a leak in the membrane. Such integrity testing methods are often referred to as air leak tests and examples are discussed in U.S. Pat. No. 5,353,630 to Soda et al. and in International Patent Application No. PCT/FR97/00930 (corresponding to International Publication No. WO 97/45193) assigned to OTV Omnium de Traitements et de Valorisation of France. In U.S. Pat. No. 5,353,630, the water on the feed side of a shelled membrane module is replaced with pressurized air. In International Patent Application No. PCT/FR97/00930, the feed side of an immersed, unshelled membrane module is exposed to air at atmospheric pressure by emptying a tank in which the module is immersed and then a partial vacuum is applied to the filtered water on the permeate side of the module.

In air leak tests, the trans-membrane pressure used is selected to exceed the bubble point corresponding to defects or holes whose size is of interest, i.e. whose undesirable passage requires monitoring. The bubble point is the air pressure which exceeds the surface tension of a liquid in a hole of the relevant size. The bubble point is described theoretically by the Young Laplace equation which provides the pressure difference required across a curved interface in terms of the surface or interfacial tension and the principal radii of curvature. For example, pressures of 0.3 to 1.0 bar are used to detect holes in the range of 0.5 to 2.3 $\mu$m.

In different air leak test methods, the trans-membrane pressure is controlled over time according to alternate strategies to provide an indication of the size or number of leaks. For example, in a pressure hold test ("PHT"), the flow rate of air required to maintain a certain trans-membrane test pressure is measured. In a pressure decay test ("PDT"), the rate of trans-membrane pressure change (decay) from an initial value is measured. With both tests, measured values are compared to membranes known to be free from defects. Both tests require precise air flow or air pressure sensors or both and are accordingly expensive to install.

Another problem with the PHT and PDT is that the accuracy of both tests is limited by the fact that air crosses the membrane by diffusion through water filled pores in addition to flowing through defects in the membrane. Such diffusive air flow is related to the surface area of the membrane unit being tested. In a large membrane unit (ie. with a flow capacity in the range of a thousand or more cubic metres per day), the diffusive air flow may be similar in magnitude to the air flow expected from a defect of the size being tested for. This problem makes detecting a single broken fiber difficult in a membrane unit of this size and generally limits the size of membrane units that can be properly tested with such tests. Thus, in a large municipal or industrial installation with several large membrane units connected together in a filter train, several distinct sets of membrane integrity testing apparatus are required. Thus, there is a need for an improved method and system for accurately measuring the integrity of filtering membranes.

SUMMARY OF THE INVENTION

An object of the present invention is to provide a method and apparatus for providing an integrity test for filtering membranes.

The present invention is a method and system for testing the integrity of membranes using a gas such as air subjected to a trans-membrane pressure. The air that crosses a membrane locally (i.e. on a specific unit of membranes) is collected. The volume of air collected for each membrane unit tested provides a quantified indication of the integrity of the membrane unit, since that volume is directly related to the amount and quality of leaks in the membrane unit.

In one aspect, the invention is directed at an improvement to an outside/in hollow fiber filtration system. For some systems, particularly those with immersed shell-less membrane units, the improvement includes a source of suction on the lumens of the membranes operable without producing permeate, such as a permeate pump operating in a recycle loop. For other systems, particularly those with shelled modules, the improvement includes a source of pressure on the outside of the membranes operable in the absence of water on the outside of the membranes, such as pressurized air. In both cases, an air collector is also provided to collect any air that passes from the outside of the membranes to their lumens during an integrity test. The amount of air so collected is measured and then released prior to subsequent tests.

In another aspect, the invention is directed at a method for testing the integrity of filtering membranes used, for example, to filter water. After stopping filtration, a first side of the membranes is exposed to air while a second side of the membranes remains exposed to water. A selected transmembrane pressure is created across the membranes from the first side of the membranes to the second side for a selected period of time, the selected transmembrane pressure being sufficient to force air through a potential defect of concern in the membranes. The first side of the membranes are then re-exposed to water and permeation is resumed. Air that passed through a set of membranes is collected and its amount measured. The set of membranes is chosen to produce a membrane unit of such a size that a defect of interest is distinguishable from diffusion of air through the pores of the membranes in the membrane unit. The amount of air collected from the membrane unit is related to an acceptable amount of air to indicate whether there is a defect in the membranes of the membrane unit. Preferably, air is collected individually but simultaneously from a plurality of membrane units in a filtration train. The amount of air collected from a membrane unit is compared with the amount of air collected from another membrane unit to indicate if one of the membrane units is defective.

BRIEF DESCRIPTION OF THE DRAWINGS

Embodiments of the invention will be described below with reference to the following drawings.

DETAILED DESCRIPTION OF THE INVENTION

Figure 1:
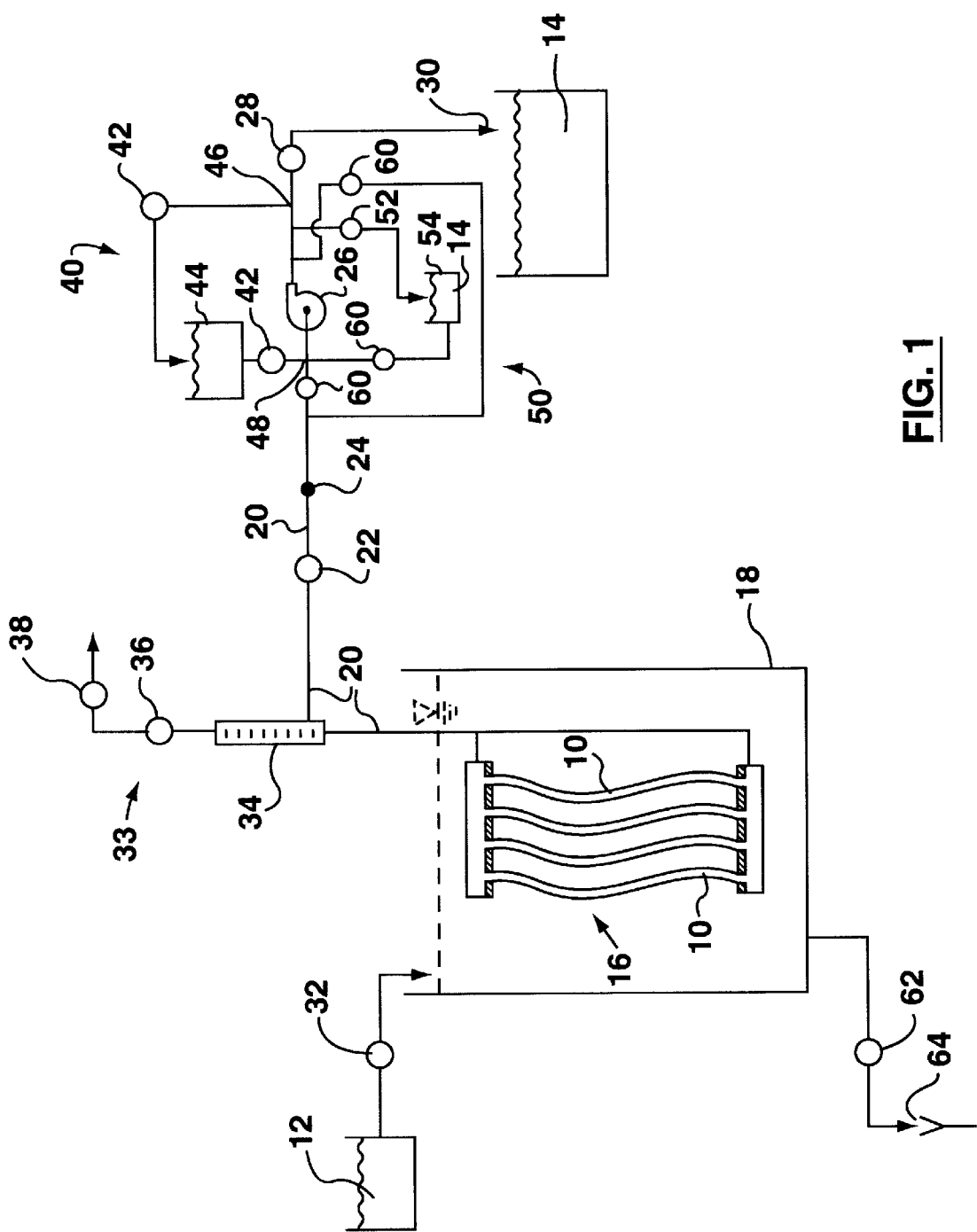
FIG. 1 illustrates integrity testing apparatus for immersed shelless outside-in flow membranes with certain components shown in elevation view.
Figure 2:
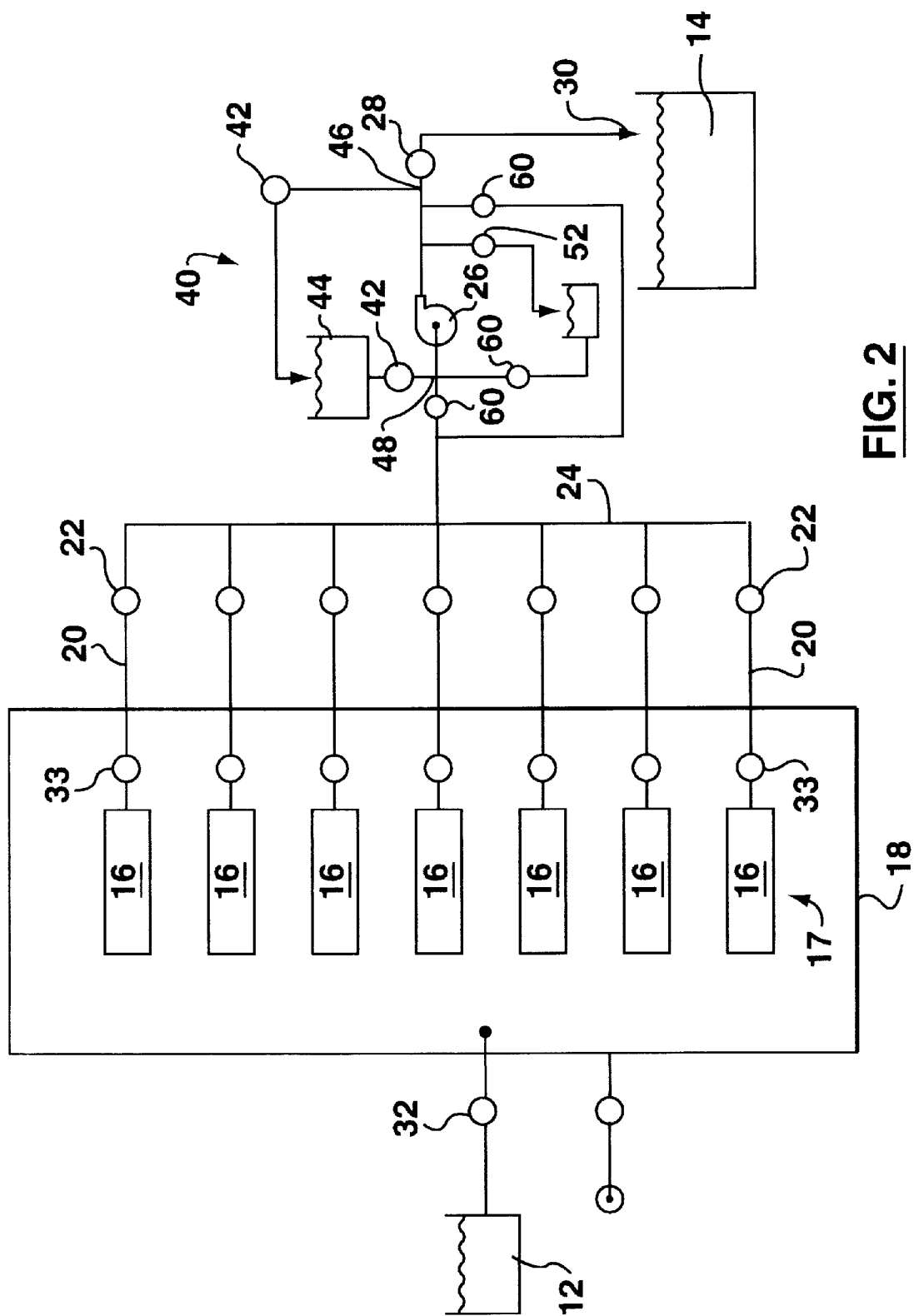
FIG. 2 illustrates integrity testing apparatus according to the embodiment of FIG. 1 with certain components shown in plan view.
Figure 3:
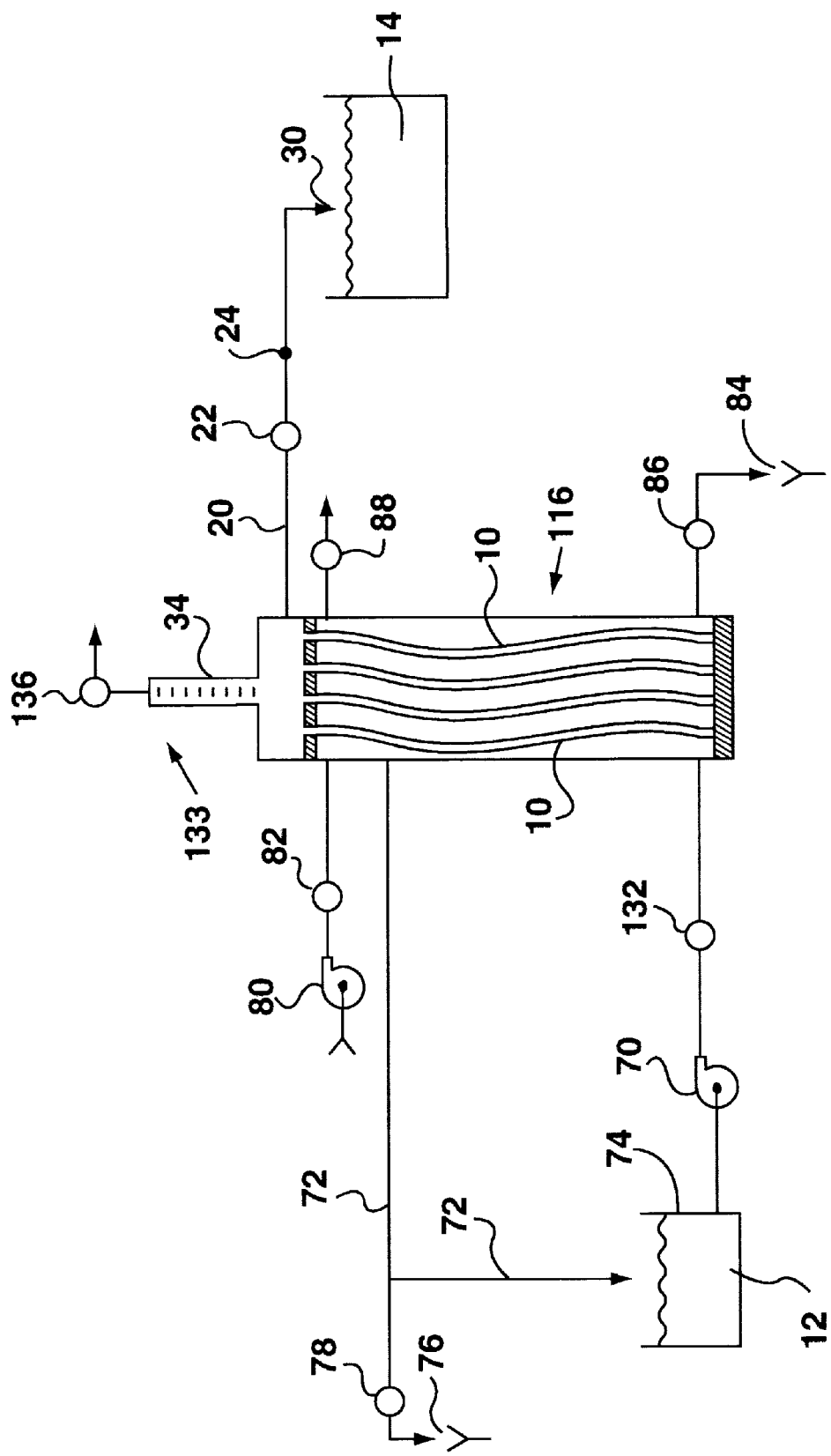
FIG. 3 illustrates integrity testing apparatus for an outside-in flow membrane module in a pressurized shell.

Referring to FIGS. 1 through 3, the embodiments described below involve hollow-fiber filtering membranes 10 which may be made of polypropylene, polysulfone derivatives, or the like. In FIG. 1 through 3, the membranes 10 are used in an outside-in ("O/I") mode. In the O/I mode, feed water 12 is applied to the outside of the membranes 10 and permeate 14 is collected from the lumens of the membranes 10. Although the description below refers to filtering water, the present invention is applicable to integrity tests of membranes used for filtering other liquids.

Referring to FIGS. 1 and 2, a plurality of membranes 10 (typically thousands) are assembled into a submerged membrane unit 16. A plurality of membrane units 16, collectively referred to as a filtration train 17, are immersed into a tank 18 and connected by permeate collection pipes 20 and an isolation valve 22 to a header 24, a permeate pump 26, an outlet valve 28 and an outlet 30. Feed water 12 enters the tank 18 through a feed valve 32. Permeation is performed by operating the permeate pump 26 to create a negative pressure in the lumens of the membranes 10. Permeate 14 is drawn out of the tank 18 through the membranes 10 and replaced by feed water 12 such that the membranes 10 remain immersed. From time to time, a permeate storage valve 52 is opened to admit permeate 14 to a storage tank 54. A backwash loop 50 has backwash valves 60 to allow the permeate pump 26 to draw permeate 14 from the storage tank 54 and flow it through the membranes 10 is a reverse direction.

To facilitate an integrity test, an air collector 33 is provided at a high point in the permeate collection pipes 20 such that air entrained in permeate 14 will collect in the air collector 33. The air collector 33 has a collection vessel 34, an air release valve 36 (also referred to as a priming valve) and a check valve 38. The bottom of the collection vessel 34 is in fluid communication with the flow of permeate 14 in the permeate collection pipes 20. The top of the collection vessel is in fluid communication with the atmosphere through the air release valve 36 and check valve 38. The collection vessel 34 is preferably a clear cylinder with graduations allowing a visual determination of volume. Optionally, the collection vessel may have a pressure gauge or sensor (not shown) and a level sensor (not shown) to allow the volume and pressure of air in the collection vessel 34 to be determined remotely or automatically by a programmable logic controller. Air release valve 36 allows air to leave the collection vessel 34 when it is under pressure while check valve 38 prevents air from entering the air collection vessel 34 from the atmosphere generally when the air collection vessel 34 is under vacuum. In place of the air release valve 36 and check valve 38, a solenoid valve and vacuum pump can be used to remove air from the collection vessel 34 when required. If so, a single vacuum pump is preferably connected by a header to a plurality of air collection vessels 34 each having its own associated solenoid valve.

Also provided is a recycle loop 40 having a loop inlet 46, a loop outlet 48, loop closure valves 42 and a loop tank 44. The loop inlet 46 is located at the discharge side of the permeate pump 26 and the loop outlet is located at the inlet side of the permeate pump 26. Thus the permeate pump 26 can be operated to produce a vacuum in the lumens of the membranes 10 without producing permeate 14. In many cases, the ordinary permeate pump 26 may not produce sufficient vacuum without cavitation or the cost of operating the permeate pump 26 to test the membranes exceeds the cost of purchasing a separate vacuum pump for testing the membranes. In these cases, it would be preferably to include a valve operable to disconnect the permeate pump 26 from the header 24 and connect instead a separate vacuum pump (with necessary apparatus) or other apparatus suitable for producing a vacuum without flow of permeate 14.

To perform an integrity test, the following steps are performed:

1. Permeation is stopped by stopping the permeate pump 26.

2. Any air (from degassing as a result of the drop in pressure across the membrane etc.) in the collection vessel 34 is discharged. This may be done by backwashing the filtration train 17 at a pressure that exceeds the minimum pressure at which the air release valve 36 will vent the collection vessel 34, by opening a solenoid valve during backwash (if one is used in place of the air release valve 36) or by opening a solenoid valve and operating a vacuum pump to overcome the suction of the permeate pump 26 during permeation. The latter method is preferred in systems where backwashing is likely to leave air bubbles in the lumens of the membranes 10 in sufficient amount to interfere with the integrity test.

3. The outside of the membranes 10 are exposed to air by opening a drain valve 62 connected to a drain 64 to at least partially empty the tank 18. The membranes 10 are not allowed, however, to dry out and their pores remain wet. Where the tank 18 is periodically deconcentrated by draining it and re-filling it with fresh feed water 12, the integrity test is preferably performed during such a deconcentration to avoid the need for an additional draining of the tank 18.

4. A transmembrane pressure is created across the membranes 10. This is done by closing the outlet valve 28, opening the loop closure valves 42 and operating the permeate pump 26. This creates a suction in the lumens of the membranes 10. The speed of the permeate pump 26 is selected such that the suction is sufficient to draw an appreciable amount of air through a defect of a relevant size according to calculations which are known to those skilled in the art. The suction is not sufficient, however, to overcome surface tension across the pores of the membranes 10 which retains the permeate 14 in the lumens of the membranes 10 or exceed the bubble point of a membrane 10 without defects. Typical transmembrane pressures may range from 20 to 90 kPa. The preferred duration of this step is selected with regard to the size of the collection vessel 34. At the end of this step, the loop closure valves 42 are closed and the permeate pump 32 is stopped.

5. Air is purged from the outside of the membranes 10 by closing the drain valve 62 and opening the feed valve 32 to refill the tank 18.

6. Permeation is resumed at a low flux by opening the outlet valve 28 and operating the permeate pump 26 at an appropriate speed. Air that passed through the membranes 10 is entrained with the flow of permeate 14 until it reaches the collection vessels 34. The air separates from the permeate 14 in the collection vessels 34 and collects in them.

7. Permeation is stopped and pressures in the permeate collection pipes 20 associated with the various membrane units 16 of the filtration train 17 are allowed to equilibrate. With equal pressure in the permeate collection pipes 22, the volume or air in one collection vessel 34 compared to another is related to the integrity of the associated membrane units 16.

8. The volume, and optionally the pressure, of the air in each collection vessel 34 is read and recorded manually or automatically.

9. Membrane units 16 associated with collection vessels 34 with unacceptable amounts of air are isolated from the filtration train 17 by closing their associated isolation valve 22.

10. Air in the collection vessel 34 is discharged by any of the techniques described in step 2 above.

11. Regular permeation is resumed.

Steps 6 and 7 above increase the accuracy of the procedure but may not be necessary in all systems. Particularly where a membrane unit 16 and its associated permeate collection pipes 20 are small, enough air may be collected in a portion step 4 alone to indicate a defect. If so, step 8 may be replaced by measuring the volume of air collected during a selected interval of time during step 4 while the membranes 10 are still subject to a transmembrane pressure during step 4. The volume collected for a membrane unit 16 may be converted to a volume at standard conditions (assuming that the transmembrane pressure applied is reasonably accurately known) or compared to air volumes collected from other membrane units 16.

With collection vessels 34 associated with each membrane unit 16, many membrane units 16 can be tested separately but simultaneously and with a single recycle loop 40 and permeate pump 26. Preferably, a large municipal or industrial filtration train 17 is divided into at least ten distinct membrane units 16. In this way, if one of the membrane units 16 is found to be defective there is at most a 10% drop in production of permeate 14 when it is isolated from the filtration train. Further, it is preferable to make each membrane unit 16 small enough that a defect of the relevant size is distinguishable from diffusion. This preferred size limit varies for different membranes 10 but typically corresponds with a capacity to produce a few thousand m$^3$day of permeate 14 or about 6000 m$^2$ of membrane surface area. Such membrane units 16 typically comprise a plurality of sub-units, often referred to as modules. Various pipes typically connect permeate 14 collected from each sub-unit to the permeate collection pipes 20 serving the entire membrane unit 16. These various pipes are preferably clear. In this way, if a defective membrane unit 16 is identified, visual inspection of the clear pipes during an integrity test is often sufficient to locate a defective sub-unit within a membrane unit 16. Once identified, a defective membrane unit 16 or sub-unit is isolated and either repaired or replaced.

The volume of air collected for each membrane unit 16 may be interpreted directly to indicate the presence or size of a defect using calculations known to those skilled in the art. Alternatively or additionally, the volume of air collected relating to one membrane unit 16 can be compared to the volume of air collected from another membrane unit 16 or, preferably, from several other membrane units 16. Provided that the pressure in the various the collection vessels 34 is constant, there is no need to know the pressure as is required to perform calculations relating the volume collected to the presence or size of defects.

Now referring to FIGS. 3, an embodiment of the invention is shown in which a plurality of membranes 10 (typically thousands) are assembled into a shelled second membrane unit 116. To avoid repetition, process steps or components will not be described specifically with reference to FIG. 3 where they are similar to process steps or components discussed with reference to FIGS. 1 and 2 or generally known. Further, names and numbers identifying components in the embodiment of FIGS. 1 and 2 may be used for similar components in the following description of the embodiment of FIG. 3. For example, only a single second membrane unit 116 is shown in FIG. 3 whereas each such second membrane unit 116 typically comprises several sub-units and a plurality of second membrane units 116 are typically connected together into a filtration train in a manner analogous to that shown in FIG. 2.

During permeation, a feed pump 70 pumps feed water 12 through a second feed valve 132 into the second membrane unit 116. Permeation is performed in O/I mode by operating the feed pump 70 to create a positive pressure on the outside of the membranes 10. Permeate 14 is produced in the lumens of the membranes under some residual pressure and flows to permeate collection pipes 20. Feed water 12 which does not pass through the membranes 10 exits the second membrane module 116 through a recycle line 72 and may be returned to a feed supply 74, or to a recycle drain 76 through a recycle drain valve 78 or partially to both.

A second air collector 133 is provided at the top of the second membrane unit 116 or at a high point in the permeate collection pipes 20 such that air entrained in permeate 14 will collect in the second air collector 133. The second air collector 133 has a collection vessel 34 and a solenoid valve 136. The bottom of the collection vessel 34 is in fluid communication with the flow of permeate 14. The solenoid valve 136 is operable to open the top of the collection vessel 34 to atmosphere and many other types of valves could also be suitable. Also provided is an air source 80, an air inlet valve 82, a secondary drain 84, a secondary drain valve 86 and a vent valve 88. The air source 80 is operable to provide pressurized air (typically, instrument air) and, although not shown, preferably services several second membrane units 116.

To perform an integrity test, the steps described below are performed. As above, steps 6 and 7 may be optional for some systems.

1. Any air in the collection vessel 34 is discharged by opening the solenoid valve 136 briefly during permeation.

2. Permeation is stopped by stopping the feed pump 70 and closing the second feed valve 132.

3. The outside of the membranes 10 are exposed to air by opening secondary drain valve 86 and operating air source 80 to flow water in the second membrane unit 116 out the secondary drain 84. While the term air is used in this description, other gases, for example nitrogen, can also be used. This step may also be performed without a secondary drain 84 by operating air source 80 to force feed water 12 in the second membrane unit 116 through the membranes 10.

4. A transmembrane pressure is created across the membranes 10. This is done by closing secondary drain valve 86 and operating air source 80 to provide air at a selected pressure in the second membrane unit 116.

5. Air is purged from the outside of the membranes 10 by opening vent valve 88 and second feed valve 132 and operating feed pump 70 to re-fill the second membrane unit.

6. Permeation is resumed at a low flux by closing the vent valve 88 and operating the feed pump 70 at a reduced speed.

7. Permeation is stopped and pressures across the various second membrane units 116 of a filtration train are allowed to equilibrate.

8. The volume, and optionally the pressure, of the air in each collection vessel 34 is read and recorded manually or automatically.

9. Second membrane units 116 associated with collection vessels 34 with unacceptable amounts of air are isolated from a filtration train by closing their associated isolation valve 22.

10. Regular permeation is resumed.

11. Air in the collection vessel 34 is discharged by opening the solenoid valve 136.

Figure 4:
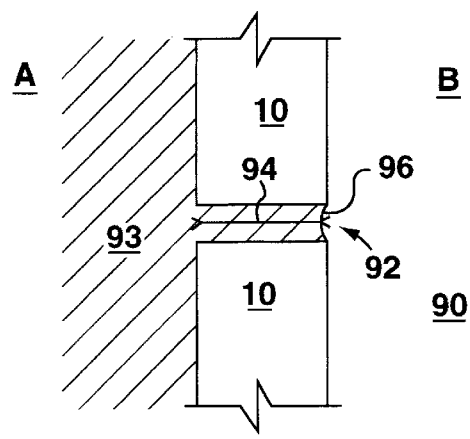
FIGS. 4, 5 and 6 illustrate cross sections of membranes showing water in or around the pores during an integrity test.
Figure 5:
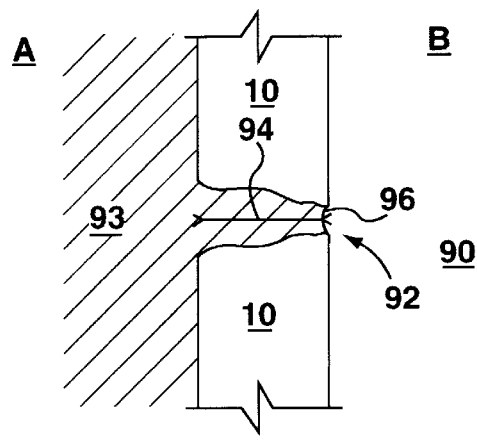
Figure 6:
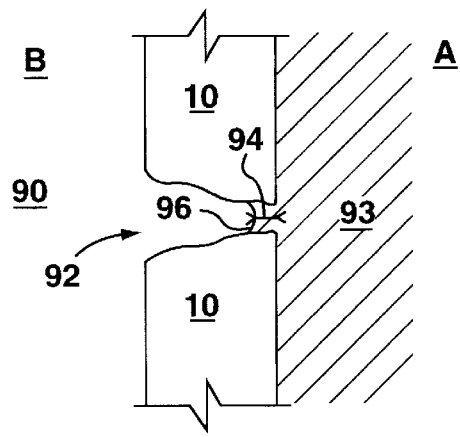

It will be apparent to those skilled in the art that the equipment and methods described above can be adapted to other sorts of membranes and other configurations of membrane units. In doing so, the inventors caution that some adaptations are preferably used only when the membranes 10 have symmetrical pores. With reference to FIGS. 4, 5 and 6, the rate of diffusion of air 90 through water 93 in the pores 92 of the membranes 10 increases as the length of the path of diffusion 94 decreases. FIG. 4 illustrates a symmetrical pore 92. The path of diffusion 94 extends from a meniscus 96 of the water 93 to the other side of the membrane 10 regardless of which side of the membrane 10 is the air 90 side. In FIG. 5, the membrane 10 has an asymmetrical pore 92 with the smaller side of the pore 92 meeting the air 90. As the transmembrane pressure is applied from air 90 side to water 93 side, a meniscus 96 forms on the air 90 side of the membrane and the path of diffusion 94 again extends substantially across the membrane 10. In FIG. 6, however, the membrane 10 has an asymmetrical pore 92 with the smaller side of the pore 92 meeting the water 93. As the transmembrane pressure is applied from air 90 side to the water 93 side, a meniscus 96 forms at a point inside the pore 92 where the surface tension of the meniscus 96 balances the transmembrane pressure. Typically, the path of diffusion 94 extends only part of the way across the membrane 10. Returning to FIGS. 1 through 3, with asymmetric hollow fiber membranes 10, the pores typically widen along a path from the outsides of the membranes 10 to their lumens. When the transmembrane pressure in the integrity test is applied from the feed side of the membranes 10 to the permeate side of the membranes 10 by either of the methods described in relation to FIGS. 1 and 2 or 3, the situation is as shown in FIGS. 4 or 5. In developing alternate embodiments, the situation shown in FIG. 6 is preferably avoided or the maximum size of a membrane unit reduced from the values suggested above to compensate for the increased rate of diffusion.

EXAMPLE

A pilot plant was constructed generally as shown in FIGS. 1 and 2 but using four membrane units each made of horizontal asymmetric hollow fiber membranes having a total of 9 $m^2$ of surface area. Three of the four membrane units were purposely made defective as described in the table below. The fourth had no defects. The cleaning regimen for the membrane unit included backwashing it once a day with a chemical cleaner into an empty tank. While the tank was empty for cleaning, an integrity test was performed generally as described above. Transmembrane pressure for the test was set at three different values (as shown in the table below) and maintained within 5% of the values given below by using a feedback signal from a pressure transducer to a control valve on the discharge side of the permeate pump. Air was collected for ten minutes and the height of the air column collected in the collection vessel was measured with a capacitance level probe while the system was still under suction. The air collection vessel has a 25 mm diameter tube but the inventors believe that a 50 mm diameter tube would have provided good resolution while providing more space for the level probe.

The pressure and temperature at the time of the height reading were recorded and, in combination with the cross sectional area of the collection vessel, allowed the height readings to be converted to an air volumes at standard conditions, which air volumes are given in the table below.

| Transmembrane Pressure (kPa) | Volume for Unit #1 - One cut fibre | Volume for Unit #2 - Two pin holes in one fibre | Volume for Unit #3 - One pin hole in one fibre | Volume for Unit #4 - No defects |
|---|---|---|---|---|
| 28 | 4820 mL | 400 mL | 150 mL | 0 mL |
| 55 | Volume too high to measure accurately | No data | 280 mL | 0 mL |
| 62 | Volume too high to measure accurately | No data | 350 mL | 0 mL |

In the trial at 62 kPa, no air was collected from Unit #4 after over twenty minutes of suction. This result suggests that the testing method of the present invention should be sufficiently sensitive to detect a single broken fiber or pin hole in a large commercial membrane unit typically having about 6,300 m$^2$ of surface area. In contrast, the same four membrane units were tested with a pressure decay test using pressurized air in the lumens of the fibres. At a transmembrane pressure of 55 kPa, for example, the pressure drop over two minutes was about 0.5 kPa for unit #4 with no defects. The pressure drop for unit #1 with a cut fiber was about 47 kPa. Using this value as a basis for calculations, the pressure drop for a single cut fiber in a 6,300 m$^2$ membrane unit would be only 0.02 kPa which would be difficult to detect against the pressure drop caused by movement of air through the wet pores of the membranes.

While preferred embodiments of the present invention have been described, the embodiments disclosed are illustrative and not restrictive, and the invention is intended to be defined by the appended claims.

We claim:

1. A method of testing the integrity of membranes used to filter a liquid feed applied to a first side of the membranes to produce a liquid permeate at a second side of the membranes comprising the steps of:
    a) providing a membrane unit to be tested;
    (b) providing an air collection vessel in fluid communication with the second side of the membranes of the membrane unit;
    (c) stopping filtration through the membrane unit;
    (d) exposing the first side of the membranes in the membrane unit to air;
    (e) retaining liquid permeate at least between the second side of the membranes and the air collection vessel;
    (f) creating a transmembrane pressure from the first side of the membranes to the second side of the membranes for a selected period of time, the transmembrane pressure being sufficient to pass air into the liquid permeate between the second side of the membranes and the air collection vessel through a potential defect of concern in the membranes but not sufficient to exceed the bubble point of a membranes without defects;
    (g) separating air which passes through the membrane unit during at least a part of step (f) above from the retained liquid permeate and collecting the separated air in the air collection vessel;
    (h) measuring the volume of air collected in step (g) above; and,
    (i) interpreting whether the measured volume of air indicates that there is a defect in the membranes of the membrane unit.

2. The method of claim 1 wherein the air is applied to a feed side of hollow fiber membranes normally operated in an O/I mode.

3. The method of claim 2 wherein the membranes have asymmetrical pores which widen towards the lumens of the membranes.

4. The method of claim 1 wherein the membranes are normally immersed during filtration in an open tank and operated in an O/I mode, the first side of the membranes is exposed to air by draining the tank and the transmembrane pressure is applied by applying a suction to the retained liquid permeate.

5. The method of claim 4 wherein the step of exposing the first side of the membranes to air by draining the tank coincides with a time in a filtration cycle at which the tank is drained to deconcentrate its contents where the tank is drained to deconcentrate its contents is done at least as frequently as the membranes are tested.

6. The method of claim 4 wherein the step of exposing the first side of the membranes to air by draining the tank coincides with a time in a filtration cycle at which the tank is drained to clean the membranes, where such cleaning is done at least as frequently as the membranes are tested.

7. The method of claim 4 wherein the air collection vessel is located at the top of the membrane unit or at a high point in a pipe connected to the membrane unit such that air entrained in the retained liquid permeate will collect in the air collection vessel.

8. The method of claim 7 wherein the air collection vessel has a valve which allows air to be released from the air collection vessel at a pressure above atmospheric and further comprising the step of discharging any air in the air collection vessel and filling the air collection vessel with liquid permeate prior to step (f) by backwashing the membrane unit through the pipe.

9. The method of claim 1 further comprising the step of discharging any air in the air collection vessel and filling the air collection vessel with liquid permeate prior to step iv.

10. In a filtration system comprising;
    (a) a tank for holding water to be filtered;
    (b) an inlet for feed water into the tank;
    (c) membranes normally immersed during permeation, the outsides of the membranes in communication with the water in the tank;
    (d) a liquid permeate pump in fluid communication with a permeate collection pipe in fluid communication with the inside of the membranes operable to apply a suction to liquid permeate in the permeate collection pipe and thereby create a transmembrane pressure across the membranes for removing a filtered permeate from the tank; and,
    (e) an outlet for retentate from the tank; the improvement comprising,
        (i) a recycle loop having a loop inlet in communication with the discharge side of the permeate pump, a loop outlet in communication with the inlet side of the permeate pump and an open tank in communication with the loop inlet and loop outlet wherein the permeate pump is operable within the recycle loop to produce a source of suction on liquid permeate in the permeate collection pipe without producing permeate to produce a suction relative to atmospheric pressure greater than the bubble point of a defect in the membranes; and (ii) an air collector in fluid communication with a high point in the permeate collection pipe and operable to collect and release air that passes from the outside of the set of membranes to the permeate collection pipe and which permits the volume of air collected to be measured, wherein the set of membranes is chosen to produce a membrane unit of such a size that a defect of interest is distinguishable from diffusion of air through the pores of the membranes in the membrane unit.

11. The system of claim 10 having a single permeate pump operable in a recycle loop connected to a plurality of membrane units and a plurality of air collectors, at least one air collector associated with each membrane unit.

12. A method of testing the integrity of membranes used to filter a liquid feed applied to a first side of the membranes to produce a liquid permeate at a second side of the membranes comprising the steps of:

(a) dividing the membranes into one or more membrane units, each membrane unit being of such a size that a defect of interest is distinguishable from diffusion of air through the pores of the membranes in the membrane unit;

(b) for each membrane unit, providing an air collection vessel in fluid communication with the second side of the membranes; and, (c) for each membrane unit to be tested,
  i) stopping filtration through the membrane unit;
  ii) exposing the first side of the membranes in the membrane unit to air;
  iii) retaining liquid permeate at least between the second side of the membranes and the air collection vessel;
  iv) creating a transmembrane pressure from the first side of the membranes to the second side of the membranes for a selected period of time, the transmembrane pressure being sufficient to pass air into the liquid permeate between the second side of the membranes and the air collection vessel through a potential defect of concern in the membranes but not sufficient to exceed the bubble point of a membranes without defects,
  v) separating air which passes through the membrane unit during at least a part of step c) iv) above from the retained liquid permeate and collecting the separated air in the air collection vessel;
  vi) measuring the volume of air collected in step b) v) above; and,
  vii) interpreting whether the measured volume of air indicates that there is a defect in the membranes of the membrane unit, wherein air is collected individually from a plurality of membrane units all subjected simultaneously to the same transmembrane pressure, and the step of interpreting whether the measured volume of air from a first membrane unit indicates that there is a defect in the first membrane unit includes comparing the measured volume of air from the first membrane unit to a measured volume of air from another membrane unit while the pressure of the liquid permeate in fluid communication with the air collection vessel of the first membrane unit is equilibrated with the pressure of the liquid permeate in fluid communication with the air collection vessel of the other membrane unit.

13. A method of testing the integrity of membranes used to filter a liquid feed applied to a first side of the membranes to produce a liquid permeate at a second side of the membranes comprising the steps of:

a) providing a membrane unit to be tested;

(b) providing an air collection vessel in fluid communication with the second side of the membranes of the membrane unit;

(c) stopping permeation through the membrane unit;

(d) exposing the first side of the membranes in the membrane unit to air;

(e) retaining liquid permeate at least between the second side of the membranes and the air collection vessel;

(f) creating a transmembrane pressure from the first side of the membranes to the second side of the membranes for a selected period of time, the transmembrane pressure being sufficient to pass air into the liquid permeate between the second side of the membranes and the air collection vessel through a potential defect of concern in the membranes but not sufficient to exceed the bubble point of a membranes without defects;

(g) re-applying feed to the first side of the membranes and creating a transmembrane pressure from the first side of the membranes to the second side of the membranes for a selected period of time, the transmembrane pressure being sufficient to pass permeated feed into the retained liquid permeate;

(h) separating air which passes through the membrane unit during at least a part of steps (f) and (g) above from the retained liquid permeate and collecting the separated air in the air collection vessel;

(i) measuring the volume of air collected in step (h) above; and, (j) interpreting whether the measured volume of air indicates that there is a defect in the membranes of the membrane unit.

14. The method of claim 13 wherein the membranes are normally immersed during filtration in an open tank and operated in an O/I mode, the first side of the membranes is exposed to air by draining the tank and the transmembrane pressure is applied by applying a suction to the liquid permeate.

15. The method of claim 13 further comprising the step of discharging any air in the air collection vessel and filling the air collection vessel with liquid permeate prior to step (f).

* * * * *